United States Patent [19]
Johnson

[11] Patent Number: 4,718,413
[45] Date of Patent: Jan. 12, 1988

[54] BONE CUTTING GUIDE AND METHODS FOR USING SAME

[75] Inventor: Wesley Johnson, Bloom, Minn.

[73] Assignee: Orthomet, Inc., Minneapolis, Minn.

[21] Appl. No.: 946,586

[22] Filed: Dec. 24, 1986

[51] Int. Cl.⁴ ............................................. A61F 5/04
[52] U.S. Cl. ........................... 128/92 VW; 128/92 VY
[58] Field of Search ...... 128/92 VW, 92 VV, 92 VY, 128/92 V, 303 R

[56] References Cited

U.S. PATENT DOCUMENTS

| | | | |
|---|---|---|---|
| D. 273,895 | 5/1984 | Kenna | D24/26 |
| D. 274,091 | 5/1984 | Kenna | D24/26 |
| D. 274,095 | 5/1984 | Kenna | D24/26 |
| 4,467,801 | 8/1984 | Whiteside | 128/303 |
| 4,474,177 | 10/1984 | Whiteside | 128/303 |
| 4,487,203 | 12/1984 | Androphy | 128/303 |
| 4,502,483 | 3/1985 | Lacey | 128/303 |
| 4,524,766 | 6/1985 | Petersen | 128/92 |
| 4,567,885 | 2/1986 | Androphy | 128/92 |
| 4,574,794 | 3/1986 | Cooke et al. | 128/92 |

OTHER PUBLICATIONS

Kenna, et al., The PCA TM Primary Total Knee System, Howmedica, Inc., Brochure No. ST 2014, 1984.
Whiteside Ortholoc TM Total Knee System, Dow Corning Wright, Brochure No. LO95-0201, 1984.

*Primary Examiner*—C. Fred Rosenbaum
*Assistant Examiner*—C. W. Shedd
*Attorney, Agent, or Firm*—James R. Haller; Mary P. Bauman

[57] ABSTRACT

Cutting guide for a bone saw used to assure accurate bone cuts in implantation of prostheses and osteotomies. A cutting guide has a main body having guide elements that include a pair of guide surfaces that engage opposite sides of a saw blade. The guide surfaces guide the blade in a predetermined plane during the cutting process. In each pair of guide surfaces, the surfaces are spaced from one another along the plane a sufficient distance to enable the saw blade to pivot out of said plane away from engagement with at least one of the guide surfaces through an angle of at least 15°. The cutting guide also includes means for attaching the guide to a bone surface to orient the guide elements with respect to the bone.

12 Claims, 7 Drawing Figures

BONE CUTTING GUIDE AND METHODS FOR USING SAME

FIELD OF THE INVENTION

The invention relates generally to the field of orthopedic surgery and particularly to orthopedic bone cutting guides.

BACKGROUND OF THE INVENTION

It is sometimes necessary for an orthopedic surgeon to perform accurate and precise bone shaping. For example, precise cutting of the femur and tibia in the area of the knee is required to shape the bone ends to receive prostheses during knee joint replacement surgery. Such preparation involves resection of (removal of bone from) the anterior, posterior and distal femoral condyles and the proximal end of the tibia. The cuts must be precisely placed so that the resulting shaped bone structure very closely fits the intended prostheses and so that the tibia and femur are properly aligned after implantation of the prosthesis. Precise bone cuts are also required when an osteotomy is performed to realign an articular joint with its physiological mechanical axis. Such preparation involves resection of a wedge of bone adjacent to the articular surface, thereby realigning the transverse axis of the joint relative to the axis of the supporting bone. The cut surfaces are planar to enable complete surface contact of the surfaces when bones are repositioned and secured in place.

At one time, shaping cuts in the bones were made without benefit of cutting guides. Surgeons attempted to correct errors made during the cutting process by application of varying quantities of cement while securing a prostheses to the bone. New orthopedic techniques include the use of porous coated prostheses. The new prostheses promote bone ingrowth; they are used with minimal or no cement. Commonly, the cement is applied in a thin layer of uniform thickness. In that case, cutting errors can no longer be easily corrected and it becomes crucial that cuts be accurately made to within a few thousandths of an inch.

The necessity for precise and accurate bone cutting has led to the development of instruments specifically designed to guide the surgeon's saw blade during the bone cutting procedure. Examples of such instruments include those sold as the Howmedica® P.C.A. TM Universal TM Total Knee Instrument System by Howmedica, Inc. Reference is made to the publication entitled "The PCA TM Primary Total Knee System", brochure No. ST2014, 1984, the teachings of which are incorporated by reference herein. Another example of instruments are those sold as the Whiteside Ortholoc TM Total Knee System by Dow Corning/Wright. Reference is made to the brochure entitled "Whiteside Ortholoc TM Total Knee System: Surgical Procedure", Form No. L095-02011, 1984, the teachings of which are incorporated by reference herein.

In one bone shaping technique, femoral cuts are made as follows: an intramedullary alignment rod is driven upwardly within the shaft of the femur for perhaps eight inches, the protruding end of the rod being used to locate precisely the cuts that are needed. Using various marking and measuring instruments, a saw guide is eventually mounted to the rod, the saw guide having slots in it through which the saw blade can extend during a sawing operation. In this manner, the distance between cuts and also the general plane of the cuts may be at least partially controlled. Unfortunately, the toothed end of the saw blade is somewhat thicker than is the body of the saw blade. To accommodate insertion of the saw blade, the slots are formed slightly wider than the thickness of the saw blade, affording the saw blade a substantial degree of freedom to wobble. The wobbling can cause cuts to be made having substantial errors in the angle of the plane of the cut. Whiteside U.S. Pat. No. 4,467,801 describes a cutting guide for a bone cutting saw blade having a slot such as the one described above. Petersen, U.S. Pat. No. 4,524,766, also describes a cutting guide for a bone cutting saw blade having slots in which a saw blade fits.

Another similar saw guide uses a flat guide surface (rather than a slot) to position and guide the saw blade. It is intended that the surgeon will maintain surface-to-surface contact between the saw blade and the planar guide surface during the cutting operation. It will be understood that bone properties vary widely; from very soft bone to very hard bone, including patches of soft bone within a hard bone structure. Hence, it is difficult to both maintain surface-to-surface contact between a saw blade and a planar guide surface and at the same time exert sufficient strength and force to appropriately cut the bone. For this reason, cuts that are made utilizing guides with flat guide surfaces sometimes are not properly positioned. Saw cutting guides having a flat guiding surface are described in the Howmedica surgical technique brochure No. ST2014, 1984 mentioned above.

SUMMARY OF THE INVENTION

This invention relates to a guide for a bone saw blade and methods for using the guide. The guide comprises a main body carrying guide elements, each element providing a pair of parallel guide surfaces adapted to guidingly and slidingly engage opposite, parallel, generally flat sides of a saw blade to guide the blade in a predetermined plane during operation of the saw when the blade is biased concurrently against both of said guide surfaces. The guide surfaces are spaced from one another generally along the plane a sufficient distance to permit the saw blade to pivot out of said plane away from engagement with at least one of the guide surfaces through an angle of at least 15°. The guide further comprises attachment means for attaching the guide to the bone to orient the guide elements with respect to the bone.

Another embodiment of the invention relates to a cutting guide for a saw blade employed to guide the blade in making pairs of spaced, parallel shaping cuts such as anterior or posterior femoral cuts, the guide including attachment means for attaching it to the bone. The cutting guide comprises a body carrying first and second sets of guide elements, each set having a pair of guide surfaces adapted to guidingly and slidingly engage opposite, parallel, generally flat sides of a saw blade to guide the blade in a predetermined plane during operation of the saw when the blade is biased concurrently against both of said guide surfaces. The guide surfaces of each set of guide elements are spaced from one another generally along the plane a sufficient distance to permit a saw blade to pivot out of said plane away from engagement with at least one of the guide surfaces through an angle of at least 15°. The guide surfaces of each set are positioned so that when the guide body is attached to a bone, e.g., the distal head of the femur, one guide surface is closer to the adjacent bone surface than the other, the one guide surface also being closer to the intramedullary canal of the bone than the other guide surface. The first and second sets of guide elements are spaced a predetermined distance from each other on the body and positioned so that the plane of the cut guided by the first set runs parallel with the plane of the cut guided by the second set. The cutting guide further comprises attachment means for attaching the guide body directly or indirectly to the bone to orient the guide elements with respect to the bone.

In another embodiment, the invention provides a cutting guide for a bone saw blade employed to guide the blade in making an anterior chamfer femoral cut or a posterior chamfer femoral cut, the guide including attachment means for attachment thereof to the femur. Chamfer cuts are front and rear cuts that are slanted at an angle of, e.g., 45° to the vertical anterior and posterior cuts previously described. The chamfer cutting guide comprises a main body and guide elements carried by the body. Each guide element provides a pair of guide surfaces adapted to guidingly and slidingly engage opposite, parallel, generally flat sides of the saw blade to guide the blade in a predetermined plane during operation of the saw. The guide surfaces of each pair are spaced from one another a sufficient distance generally along the plane to enable the saw blade to pivot out of said plane away from engagement with at least one of the guide surfaces through an angle of at least 15°, one guide surface being positioned closer to the bone surface than the other when the guide is attached to the femur. The planes delivered by each pair of guide surfaces intersect at a point above the bone surface.

The invention in another embodiment provides a method of accurately shaping a bone by means of accurate saw cuts. The method employs a saw blade guide having a main body carrying guide elements, said guide elements providing a pair of guide surfaces adapted to guidingly and slidingly engage opposite, parallel, generally flat sides of a saw blade to guide the blade in a predetermined plane during operation of the saw. The guide surfaces are spaced from one another generally along the plane a sufficient distance as to enable the saw blade to pivot out of said plane away from engagement with at least one of the guide surfaces through an angle of at least 15°. The method comprises the steps of orienting and attaching the guide to a bone, inserting a saw blade between the guide surfaces of the guide elements, urging the saw blade into sliding contact with both of the guide surfaces while activating the saw blade to cut the bone, and removing the saw blade from the cutting guide by pivoting the blade out of the plane and away from engagement with at least one of the guide surfaces.

DETAILED DESCRIPTION OF THE PREFERRED EMBODIMENTS

Six basic bone cuts are required in a typical surgical protocol to prepare the tibia and femur to receive knee replacement prostheses. The six cuts include a proximal tibial cut (FIG. 1), a distal femoral cut (FIG. 2), anterior and posterior femoral cuts (FIG. 3), and anterior and posterior femoral chamfer cuts (FIG. 4). Each basic bone cut will generally require different bone cutting guides; however, appropriate attachment devices may be devised to permit use of a single guide for several cutting operations.

Figure 1:
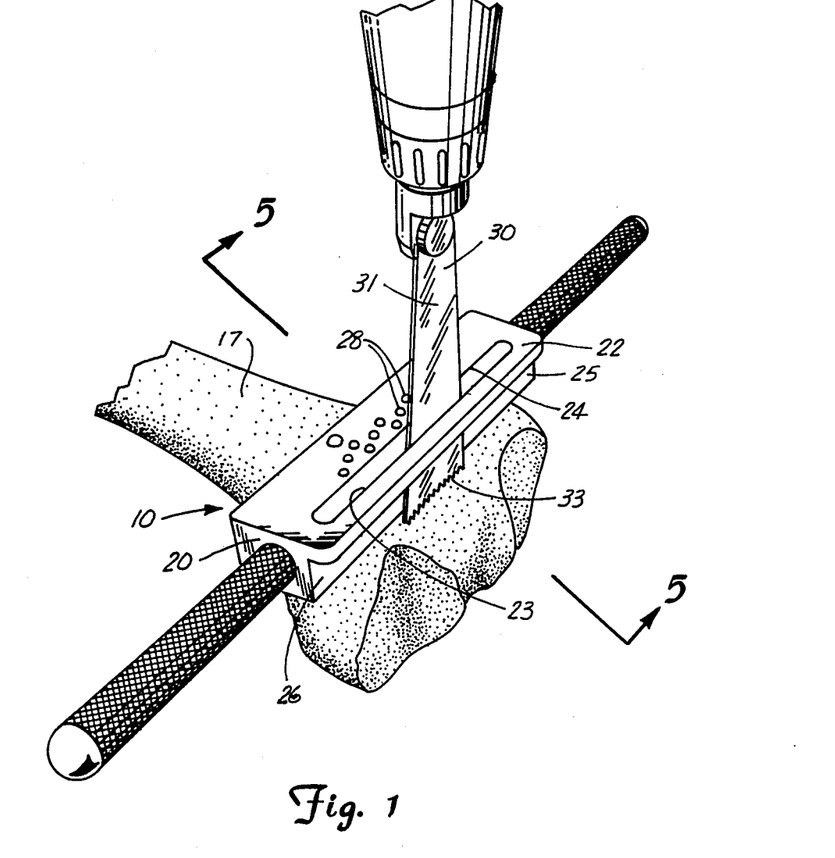
FIG. 1 is a perspective view of a cutting step of the invention being positioned on the anterior surface of the proximal tibia.
Figure 5:
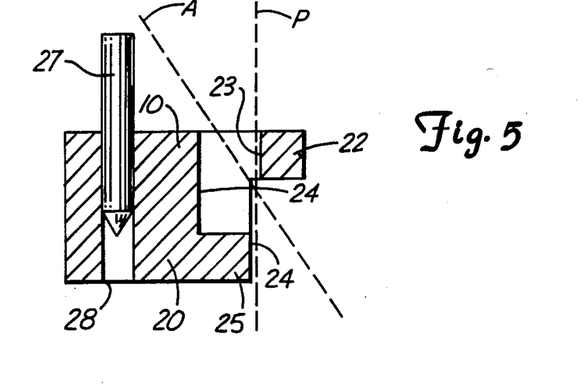
FIG. 5 is a cross-sectional view of the cutting guide of FIG. 1.

The bone cutting guide (10) shown in FIGS. 1 and 5 may be used to guide a saw blade (30) in the proximal tibial cut. The body (20) of the guide is positioned on the anterior surface (17) of the proximal tibia using an external alignment guide (not shown). The tibial external alignment guide is designed to establish alignment reference points at the center of the knee joint and at the center of the ankle joint and is used to orient the bone cutting guide relative to the two reference points selected. Tibial cut orientation, e.g., bone cutting guide orientation, varies with prosthetic knee design and surgeon preference. Typically, the medial/lateral orientation of the cutting plane is perpendicular to a line defined by the two reference points selected. The anterior/posterior orientation of the cutting plane may range from 0 to 12 degrees posterior slope. The alignment guide is visually aligned to be generally parallel with the axis of the tibia.

Cutting guide elements (22) and (25) providing a pair of guide surfaces (23) and (26), are carried by the body (20) of the cutting guide. The body (20) of the cutting guide is generally parallelepiped in shape, and the guide element (22) is formed as a bar extending parallel to the long dimensions of the body. The body is desirably recessed as shown at (24) to define the other guide element (25). The guide surfaces (23) and (26) face in generally opposite directions and define between them a plane P in which the saw blade moves during a sawing procedure. Using the alignment guide, cutting guide elements (22) and (25) are oriented so that one of the guide surfaces (26) is closer to the anterior bone surface than the other (23). The one guide surface (26) that is closer to the anterior surface is also mounted on the bone so that it engages the side of the saw blade facing the portion of the bone that will remain intact after resection, thus assuring that if any cutting error is made, e.g., by the blade pushing away from the guide surface elements, it will occur in the portion of the bone that will be discarded.

After the bone cutting guide is positioned on the tibia, it is secured by pins (27) received in holes (28) in the guide body (20) and aligned holes in the confronting bone surface (17), respectively. Then a cut is made by placing the saw blade between the guide surfaces (23)

and (26) so that the guide surfaces engage opposing sides of the saw blade (31) and (32). The surgeon urges the saw blade sides against the respective guide surfaces during the bone cutting operation.

After the cutting procedure has been completed the saw blade (30) may be removed by pivoting it out of the plane away from at least one of the guide surfaces (26) through a convenient angle as shown by dotted line "A" in FIG. 5 and away from the remaining cut surface of the bone so that the saw blade (30), including its wide toothed portion (33), can be withdrawn from the guide. The guide surfaces permit the blade to be pivoted through an angle of at least 15°, preferably at least 30°.

Five bone cuts are required in the exemplified protocol to prepare the distal femur to support the femoral component of a total knee prosthesis. The order of these cuts varies with surgical technique and surgeon preference. Typical femoral cuts include the distal cut, anterior cut, posterior cut, anterior chamfer cut, and posterior chamfer cut. In one sequence, a first distal cut is followed serially by the anterior, posterior and then the two chamfer cuts. A second approach begins with the anterior cut, followed by the posterior cut, distal cut, and then the two chamfer cuts. The specific cutting guides exemplified below have been developed for the former surgical approach. The concept for using these cutting guides is equally applicable to both approaches for preparing the femur.

Figure 2:
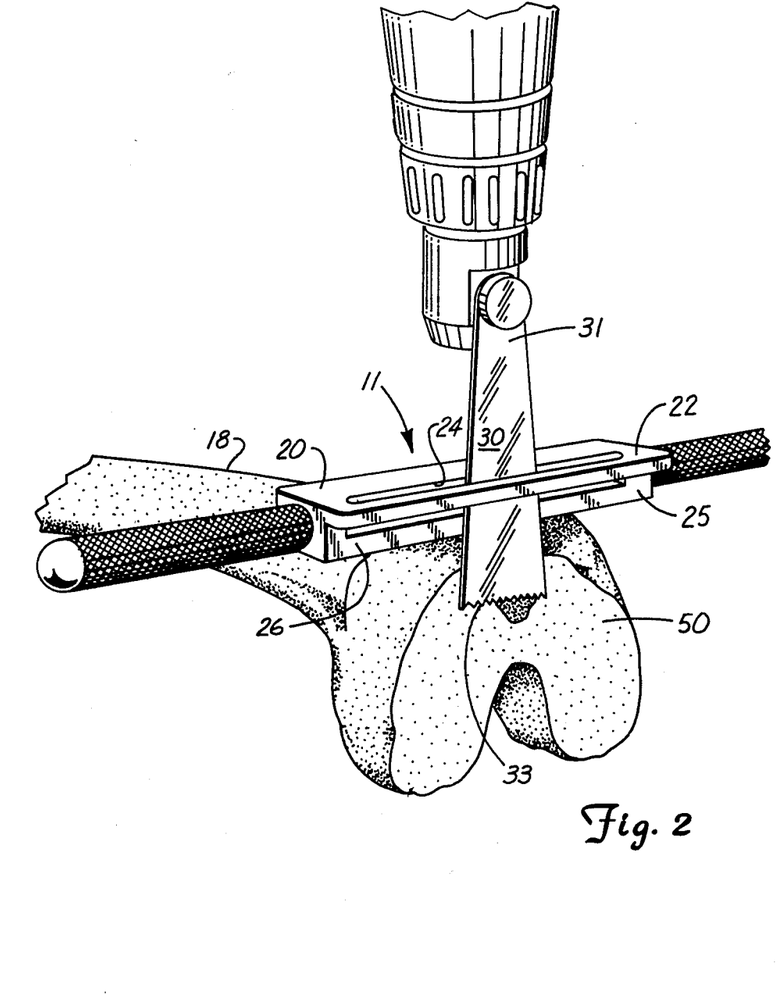
FIG. 2 is a perspective view showing a step in the performance of a distal femoral cut utilizing a guide of the invention.

The cutting guide (11) of FIG. 2 is designed to aid the surgeon in making an accurate distal femoral cut. The guide body (20) is positioned on the anterior surface (18) of the distal femur, using a femoral alignment guide (not shown). The femoral alignment guide is designed to establish orientation of the distal femoral cut relative to the femoral mechanical axis. Anatomical references include the intramedullary canal, femoral shaft, or hip joint center combined with the knee joint center. Referencing the hip joint center is preferred as this point combined with the knee joint center defines the mechanical axis of the femur. In general, the distal femoral cut is made perpendicular to the mechanical axis in both medial/lateral and anterior/posterior directions.

The guide body (20) carries guide elements (22) and (25) each having a pair of guide surfaces (23) and (26), respectively, adapted to guidingly and slidingly engage opposing sides (31) and (32) of the saw blade (30). One guide surface (26) is positioned closer to the anterior surface (18) of the femur than the other guide surface (23) when mounted on the bone. The one guide surface (26) also engages the same side of the saw blade (30) that faces the bone portion (50) intended to remain after resection.

The bone cutting guide (11) thus restrains blade travel to prevent disruption of the bone surface that will remain intact after resection. In making the actual cut the surgeon follows the procedure described above. The saw blade may then be rotated away from the preserved cut surface for removal. The guide (11) is similar to the guide (10) of FIG. 1, and is similarly held to the anterior surface (18) of the femur by means of pins or the like.

After the distal femoral cut has been made, guide holes are placed in the resulting flat remaining bone surface to support and align subsequent bone cutting guides. Alignment holes in the distal femur are located with the aid of a drill guide (not shown). The drill guide is placed flush on the distal femoral cut and centered relative to the distal femur. Guide holes in the drill guide are located to match support pegs (36) on subsequent cutting guides and attachment pegs on the femoral component of the total knee implant.

Figure 3:
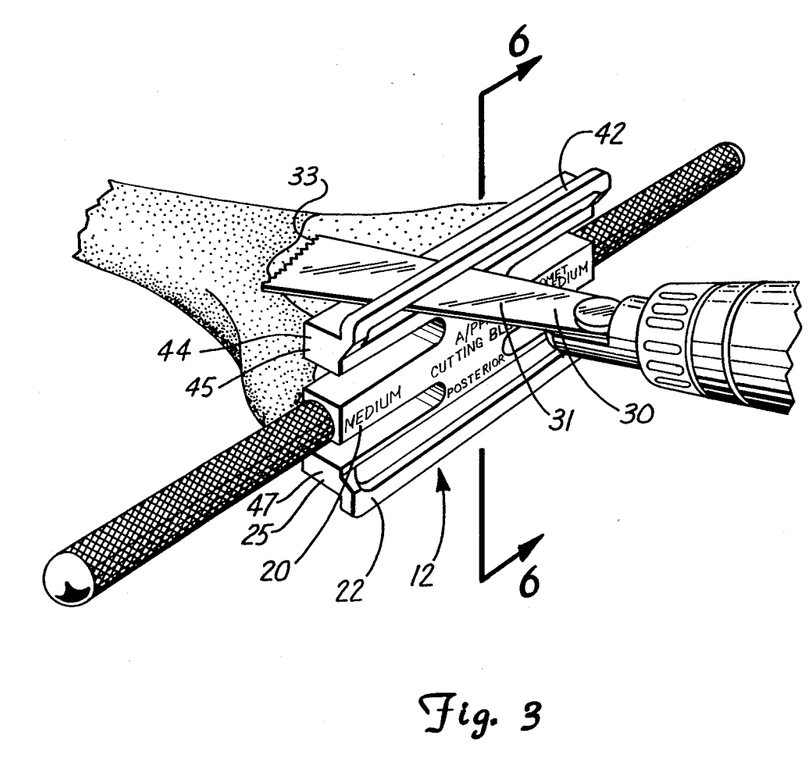
FIG. 3 is a perspective view showing a further bone cutting step, a guide of the invention being positioned on the cut surface of the distal femur positioned to guide the surgeon in making anterior and posterior femoral cuts.
Figure 4:
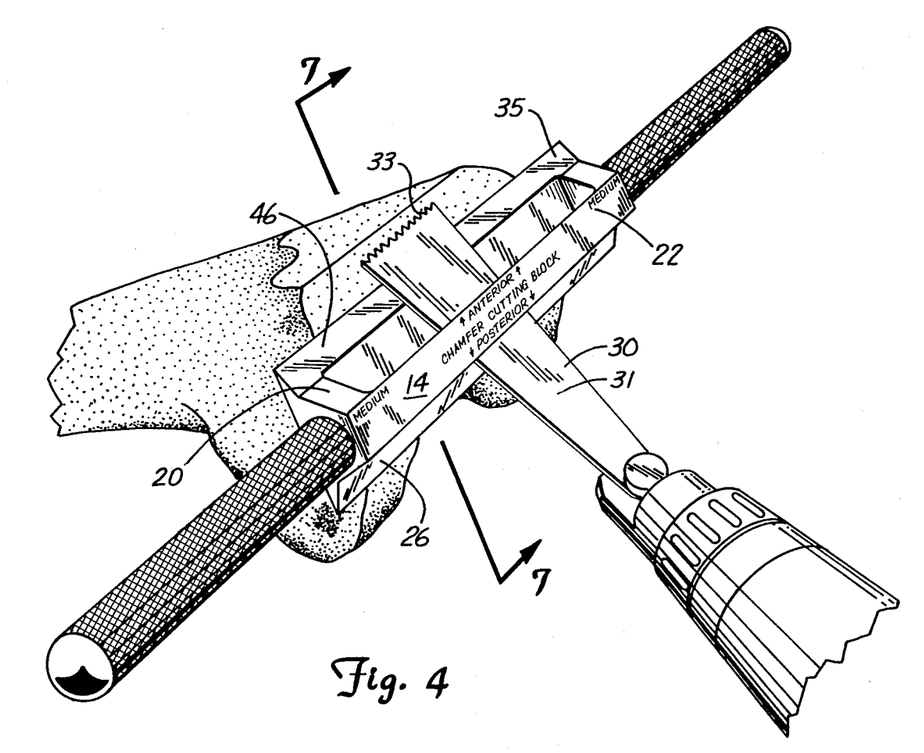
FIG. 4 is a perspective view showing the performance of a chamfer cut, a guide of the invention being positioned on the cut distal femur surface to guide the surgeon in making the anterior and posterior femoral chamfer cuts.
Figure 6:
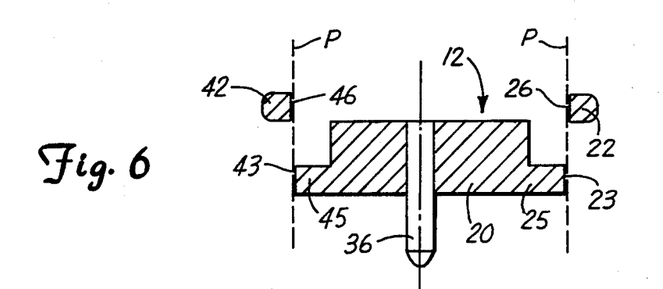
FIG. 6 is a cross-sectional view of the cutting guide of FIG. 3.

The cutting guide (12) shown in FIGS. 3 and 6 is used to make anterior and posterior femoral cuts. That guide (12) comprises a body (20) carrying first and second sets (44), (47) of guide elements (22), (25), and (42), (45), each set having a pair of guide surfaces (23), (26), and (43), (46) adapted to guidingly and slidingly engage opposite generally flat sides (31), (32) of a saw blade (30) to guide the blade (30) in a predetermined plane shown as P in FIG. 6 during operation of the saw. The guide surfaces (23), (26), and (43), (46) of each set are spaced from one another a sufficient distance as to enable the saw blade (30) to pivot through an angle of at least 15° out of said plane P away from engagement with at least one of the guide surfaces. In each set of guide elements, one guide surface (23, 43) is oriented closer to the cut surface of the femur and closer to the intramedullary canal of the femur than the other guide surface (26, 46). When the guide (12) is mounted on the bone the sets (44) and (47) of guide elements carried by the body (60) are spaced a predetermined distance apart and are positioned so that the planes shown as P (shown in FIG. 6) of blade movement defined by the guide surfaces of each element are parallel to each other. The orientation of the two cutting planes for the anterior and posterior femoral cuts determined by the placement of the guide element sets relative to the distal femoral cut, is set to match that of the mating surfaces on the femoral component of the knee implant. Four or more sizes of guides may be available for use—extra-large, large, medium, and small, with the distances between sets of guide elements ranging from approximately 55 mm when the extra-large guide is used to 44 mm when the small guide is used.

The cutting guide body (60) is attached to the bone so that one set of guide elements (44) is positioned adjacent the anterior portion of the distal femur and the other set (47) is positioned adjacent the posterior portion of the distal femur. The surgeon may then insert a saw blade (30) into one set of guide elements and resect the bone according to the procedure described above. Following that, the surgeon will make a second cut using the other set of guide elements and following the cutting procedure described above. Each set of guide elements restricts saw blade motion from disrupting the desired cut surface.

Figure 7:
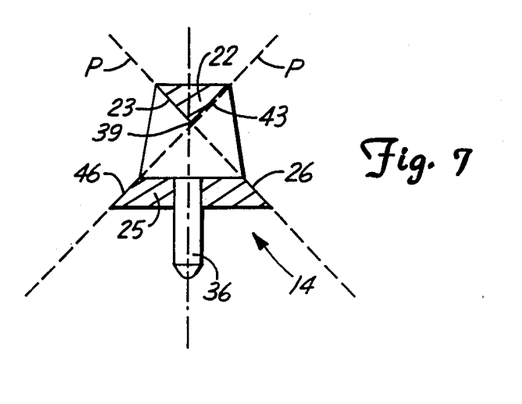
FIG. 7 is a cross-sectional view of the cutting guide of FIG. 4.

Finally, anterior and posterior chamfer cuts are made by the surgeon. A chamfer cutting guide (14) is shown in FIGS. 4 and 7 as comprising guide elements (22) and (25) providing first and second pairs of guide surfaces (23, 26), and (43, 46) adapted to guidingly and slidingly engage opposite generally flat sides of the saw blade (30) to guide the blade (30) in a predetermined plane P during operation of the saw. The pairs of guide surfaces (23, 26) and (43, 46) are spaced generally along the plane a sufficient distance from each other to enable the saw blade to pivot out of said plane away from engagement with at least one of the guide surfaces through an angle of at least 15°. The guide (14) includes attachment means (36) orienting the guide (14) so that each pair of guide surfaces includes one guide surface (26, 46) that is closer to the cut surface of the femur than the other guide surface (23, 43) when the cutting guide (14) is attached to the bone. The pairs of guide surfaces are carried by the guide body so that the plane P defined by the guide surfaces of each pair intersect at a point (39) spaced from the cut distal femur surface.

The body of the chamfer cutting guide (14) may desirably be attached to the bone by placing pins (36) in the holes made for the anterior/posterior femoral cuts. Once the guide (14) has been properly oriented and attached the surgeon makes sequential cuts using the guide elements carried by the body according to the procedure described above.

In a preferred embodiment, the chamfer cutting guide comprises a pair of parallel, generally triangular prisms having adjacent vertices and having end supports joining the prisms. The prisms have respective parallel guide surfaces laying in parallel planes and spaced so as to receive between them opposite generally flat sides of the saw blade. The cutting planes established by the two pairs of guide surfaces are aligned, relative to the distal femoral cut, to ensure uniform contact between the cut surface and the adjoining implant surface.

All the cutting guides of the invention include attachment means for securing them to the bony structure for which they will be used. Desirably the attachment means are smooth pins which may or may not be secured to the cutting guide. Other means for attaching the cutting guides include screws which may be anchored into the bony structure or a clamping mechanism that grasps the bony structure.

In one embodiment the attachment means includes pins insertable in a bone, the cutting guide having a plurality of holes sized and spaced to receive the pins. Desirably the hole is sized so that force must be applied to the guide attached to it. The close fit of the pin in the hole restrains the guide from moving during the cutting operation. In another embodiment the holes in the body spaced and sized to received the pins are in alternate positions so that the guide may be oriented in several positions with respect to the bone without adjusting the location of the pins.

The invention described herein relates to a cutting guide for a bone saw blade. Although the cutting guides described above are used primarily for total knee arthroplasty, the cutting guides may also be used with bone resection for various types of implants, including hip, ankle, shoulder, wrist, elbow and the like. The cutting guides of this invention may also be used to make general bone cuts reguired in osteotomies of long bones. The guide surfaces of the guide elements of this invention define a discrete cutting plane for saw blade motion. The orientation position of the cutting plane may be predetermined using external or internal alignment jigs and guides. The guide surfaces are so arranged with respect to the bone that during saw blade operation rotation of the saw blade about either guide element moves the cutting edge of the blade into bone which is to be resected and discarded. The guide surfaces restrain blade travel from disrupting the desired cut bone surface.

The cutting guides of this invention commonly have handles on either end of the main body that run parallel to the cutting surfaces. The handles allow the surgeon to easily move the cutting guide to position it on the bone. When the cutting guide is provided with holes that engage pins previously positioned on the bone, the handles of the guide may be grasped by the surgeon and the guide holes matched to the pins. The surgeon may then apply downward force to the handles to cause the guide body to move downwardly engaging the pins in the holes. This allows the guide to be tightly positioned on the pin so there is no movement of the guide during the cutting process.

While a preferred embodiment of the present invention has been described, it should be understood that various changes, adaptations and modifications may be made therein without departing from the spirit of the invention and the scope of the appended claims.

What is claimed is:

1. A cutting guide for a bone saw blade comprising: a body; a guide element carried by the body and having a pair of guide surfaces adapted to guidingly and slidingly engage opposite generally flat sides of a saw blade to guide the blade in a predetermined plane during operation of the saw when the blade is biased concurrently against both of said guide surfaces, said surfaces being spaced from one another generally along the predetermined plane a sufficient distance to enable the saw blade to pivot out of said plane away from engagement with at least one of the guide surfaces through an angle of at least approximately 15°; and attachment means for attaching the guide to a bone surface to orient the guide element with respect to the bone.

2. The cutting guide of claim 1 wherein the guide elements are aligned so that any undesired movement of the saw blade during the cutting operation is harmlessly in a direction toward a portion of the bone being resected and discarded.

3. The cutting guide of claim 1 for cutting a bone end having a center of mass wherein one of the guide elements carried by the body is closer to the bone surface than the other element when the guide is mounted on the bone surface, said one guide element being on the same side of said plane as is the center of mass of the bone end.

4. The cutting guide of claim 1 further comprising manually graspable handle means carried by the body for stabilizing the guide during a cutting operation.

5. The cutting guide of claim 1 wherein the attachment means includes means attachable to a bone structure and having a plurality of pins extending outwardly therefrom, said cutting guide body having a plurality of holes sized and spaced to receive said pins to orient the cutting guide with respect to the bone.

6. The cutting guide of claim 5 wherein the holes are sized and spaced to receive the pins in alternate positions so that the guide may be oriented with respect to the bone without adjusting the location of the pins.

7. The cutting guide of claim 1 wherein the attachment means includes pins insertable in a bone, said cutting guide body having a plurality of holes sized and spaced to receive said pins to orient the guide with respect to the bone.

8. The cutting guide of claim 7 wherein the holes in the body are spaced and sized to receive the pins in alternate positions so that the guide may be oriented with respect to the bone without adjusting the location of the pins in the bone.

9. A proximal tibial cutting guide for a saw blade for use in resecting a bone portion from a remaining tibia portion, comprising:
a body; a guide element carried by the body and having a pair of guide surfaces adapted to guidingly and slidingly engage opposite generally flat sides of a saw blade to guide the blade in a predetermined plane during operation of the saw when the blade is concurrently biased against both of said guide surfaces, said surfaces being spaced from one another a sufficient distance to enable the saw blade to pivot out of said plane away from engagement with at least one of the guide surfaces through an angle of at least approximately 15°; attachment means for attaching the guide to a bone surface to orient the guide elements with respect to the bone, one guide surface being closer to the bone surface when the guide is mounted on the bone than the other guide surface and the one guide surface being available to contact the side of the saw blade facing the remaining tibia portion so that any pivoting of the saw blade away from the guide element during the cutting operation will be in a direction toward the bone portion being resected.

10. An anterior/posterior femoral cutting guide for a saw blade comprising:

a body; first and second sets of guide elements carried by the body, each set having a pair of guide surfaces adapted to guidingly and slidingly engage opposite generally flat sides of the saw blade to guide the blade in a predetermined plane during operation of the saw when the blade is biased concurrently against both of said guide surfaces, said surfaces being spaced from one another a sufficient distance to enable the saw blade to pivot out of said plane away from engagement with at least one of the guide surfaces through an angle of at least approximately 15°, one of said guide surfaces being carried closer to the bone surface than the other when the guide is mounted on the bone and the one surface being adapted to engage the side of the saw blade facing the intermedullary canal of the bone, the first and second set of guide elements being spaced a predetermined distance apart on the guide body so that the first is positioned in cutting proximity with the anterior femoral condyle during cutting operation and the second set is positioned in cutting proximity with the posterior femoral condyle during cutting operation, the predetermined planes through which the blade moves being parallel to each other; and attachment means for attaching the guide to a bone surface to orient the guide elements with respect to the bone.

11. A cutting guide for use in making anterior and posterior chamfer cuts in a femur comprising:

a main body; guide elements carried by the body, and each element providing first and second pairs of guide surfaces adapted to guidingly and slidingly engage opposite parallel, generally flat sides of a saw blade to guide the blade in a predetermined plane during operation of the saw when the blade is biased concurrently against both of said guide surfaces; the guide surfaces of each pair being spaced from one another generally along the plane a sufficient distance so as to enable the saw blade to pivot out of said plane away from engagement with at least one of the guide surfaces thrugh an angle of at least 15°, one guide surface of each pair being positioned closer to a bone surface than the other when the guide is mounted on the femur, the planes of the first and second pairs of guide elements intersecting at a point spaced above a bone surface when the body is attached thereto; and attachment means for attaching the body to the bone surface to orient the guide elements with respect to the bone.

12. A method of using a cutting guide for a bone saw blade employing a main body carrying guide elements; said guide elements each providing a pair of guide surfaces adapted to guidingly and slidingly engage opposite generally flat sides of a saw blade to guide the blade in a predetermined plane during operation of the saw when the blade is biased concurrently against both of said guide surfaces, the guide surfaces being spaced generally along the plane from one another a sufficient distance as to enable the saw blade to pivot out of said plane away from engagement with at least one of the guide surfaces through an angle of at least 15°; and attachment means for attaching the body to orient the guide elements with respect to the bone;

the method comprising: orienting and attaching the guide to a bone; inserting a saw blade between the guide surfaces of the guide elements, urging the saw blade into concurrent sliding contact with the guide surfaces while activating the saw blade to cut the bone, removing the saw blade from the cutting guide by pivoting the blade out of the plane and away from engagement with at least one of the guide surfaces.

* * * * *